(12) United States Patent
Moore

(10) Patent No.: US 9,616,168 B2
(45) Date of Patent: Apr. 11, 2017

(54) MEDICAL DEVICE FOR DELIVERING AT LEAST ONE FLUID FROM A MEDICAL DEVICE

(71) Applicant: SANOFI-AVENTIS DEUTSCHLAND GMBH, Frankfurt am Main (DE)

(72) Inventor: David Moore, Leicestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/359,353

(22) PCT Filed: Nov. 30, 2012

(86) PCT No.: PCT/EP2012/074055
§ 371 (c)(1),
(2) Date: May 20, 2014

(87) PCT Pub. No.: WO2013/079643
PCT Pub. Date: Jun. 6, 2013

(65) Prior Publication Data
US 2014/0330206 A1    Nov. 6, 2014

(30) Foreign Application Priority Data
Nov. 30, 2011   (EP) ..................................... 11191263

(51) Int. Cl.
*A61M 5/142*   (2006.01)
*A61M 5/19*   (2006.01)
(Continued)

(52) U.S. Cl.
CPC ...... *A61M 5/14216* (2013.01); *A61M 5/1407* (2013.01); *A61M 5/19* (2013.01);
(Continued)

(58) Field of Classification Search
CPC ......... A61M 2005/14208; A61M 2005/31588; A61M 5/14212; A61M 5/14216;
(Continued)

(56) References Cited

U.S. PATENT DOCUMENTS 6,613,019 B2    9/2003   Munk
2009/0299328 A1   12/2009   Mudd et al.
(Continued)

FOREIGN PATENT DOCUMENTS

EP         2335755         6/2011
JP         2009-526565 A   7/2009
(Continued)

OTHER PUBLICATIONS

"dwell time." Mosby's Medical Dictionary, 8th edition. 2009. Elsevier Apr. 12, 2016 http://medical-dictionary.thefreedictionary.com/dwell+time.*
(Continued)

*Primary Examiner* — Imani Hayman
*Assistant Examiner* — James D Ponton
(74) *Attorney, Agent, or Firm* — McDonnell Boehnen Hulbert & Berghoff LLP

(57) ABSTRACT

The invention relates to a medical device and a method for delivering at least one fluid from a medical device. More particularly, the present patent application relates to medical devices for delivering at least one, in particular two drug agents from separate reservoirs. The technical problem of preventing after-dripping and at the same time improving the safety and the dose accuracy of a medical device is solved by a method for delivering at least one fluid from a medical device, wherein the fluid is ejected from a reservoir by an advancing movement of a bung, wherein an electro-mechanical device is instructed to move the bung via a piston over a predetermined distance and wherein, after a
(Continued)

dwell time following the advancing movement of the piston, the piston is retracted by the electromechanical device.

13 Claims, 8 Drawing Sheets

(51) Int. Cl.
- *A61M 5/20* (2006.01)
- *A61M 5/14* (2006.01)
- A61M 5/24 (2006.01)
- A61M 5/315 (2006.01)
- A61M 5/31 (2006.01)

(52) U.S. Cl.
CPC .......... *A61M 5/20* (2013.01); *A61M 5/31573* (2013.01); *A61M 5/24* (2013.01); *A61M 5/31546* (2013.01); *A61M 5/31583* (2013.01); *A61M 2005/14208* (2013.01); *A61M 2005/3126* (2013.01); *A61M 2005/3128* (2013.01); *A61M 2005/3152* (2013.01); *A61M 2005/31588* (2013.01); *A61M 2205/3365* (2013.01); *A61M 2205/502* (2013.01); *A61M 2205/8212* (2013.01)

(58) Field of Classification Search
CPC .. A61M 5/1422; A61M 5/20; A61M 5/31573; A61M 5/31575; A61M 5/31576; A61M 5/31578; A61M 5/3158; A61M 5/31583; A61M 5/19; A61M 5/2066; A61M 5/31596

See application file for complete search history.

(56) References Cited

U.S. PATENT DOCUMENTS

| | | | | |
|---|---|---|---|---|
| 2010/0185152 | A1* | 7/2010 | Larsen | A61M 5/1452 |
| | | | | 604/154 |
| 2012/0078222 | A1* | 3/2012 | Smith | A61M 5/14216 |
| | | | | 604/506 |
| 2012/0245560 | A1* | 9/2012 | Hochman | 604/518 |
| 2013/0041257 | A1 | 2/2013 | Nemoto | |

FOREIGN PATENT DOCUMENTS

| | | | |
|---|---|---|---|
| JP | 2011-520569 A | | 7/2011 |
| WO | 2006/084821 | | 8/2006 |
| WO | 2007/094833 | | 8/2007 |
| WO | WO2007/094833 | * | 8/2007 |
| WO | 2009/143255 | | 11/2009 |
| WO | 2011/091246 | | 7/2011 |
| WO | 2011/136218 A1 | | 11/2011 |

OTHER PUBLICATIONS

International Search Report for Int. App. No. PCT/EP2012/074055, completed Feb. 28, 2013.

Japanese Office Action for JP Application No. 2014-543904, dated Aug. 16, 2016.

\* cited by examiner

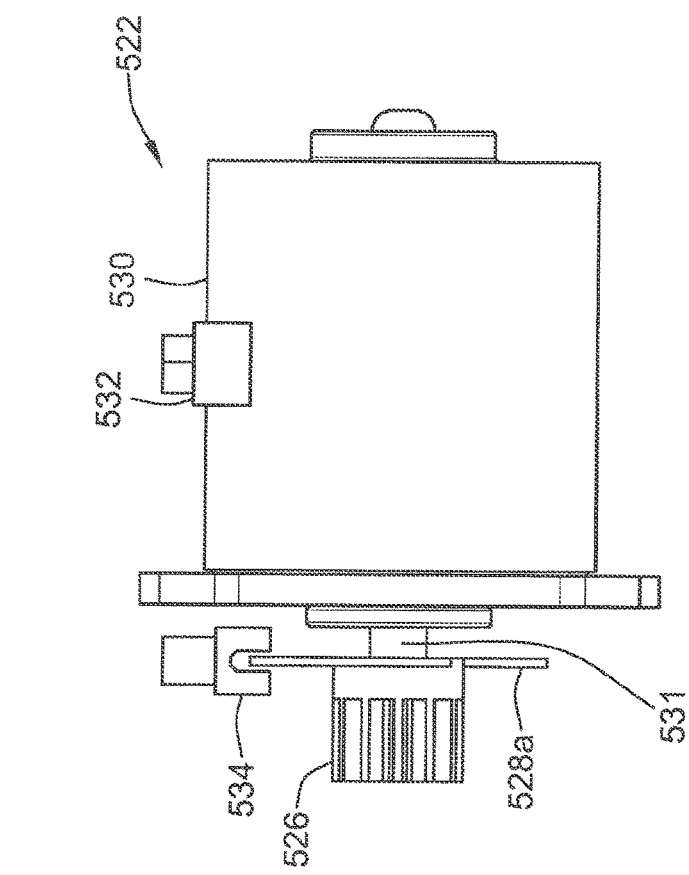
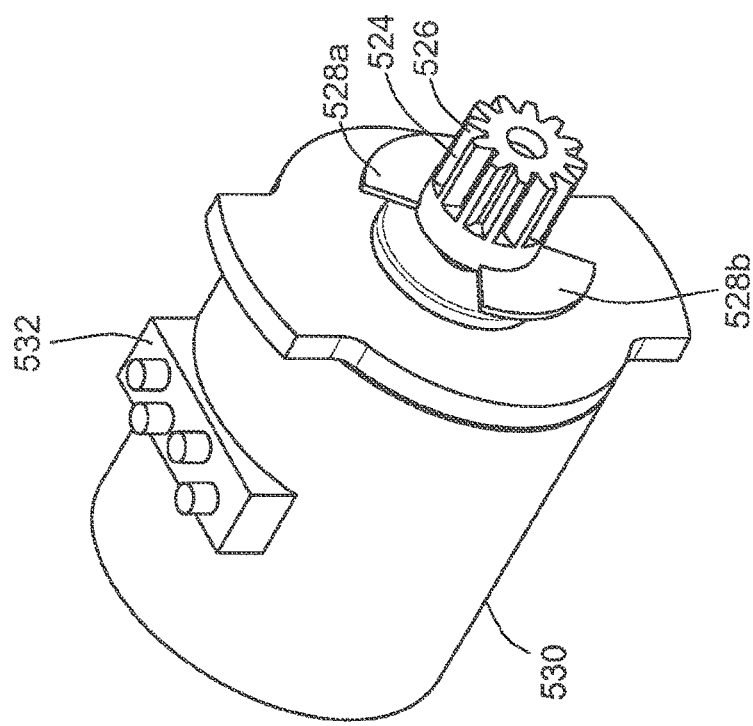
Fig.4B
Fig.4A

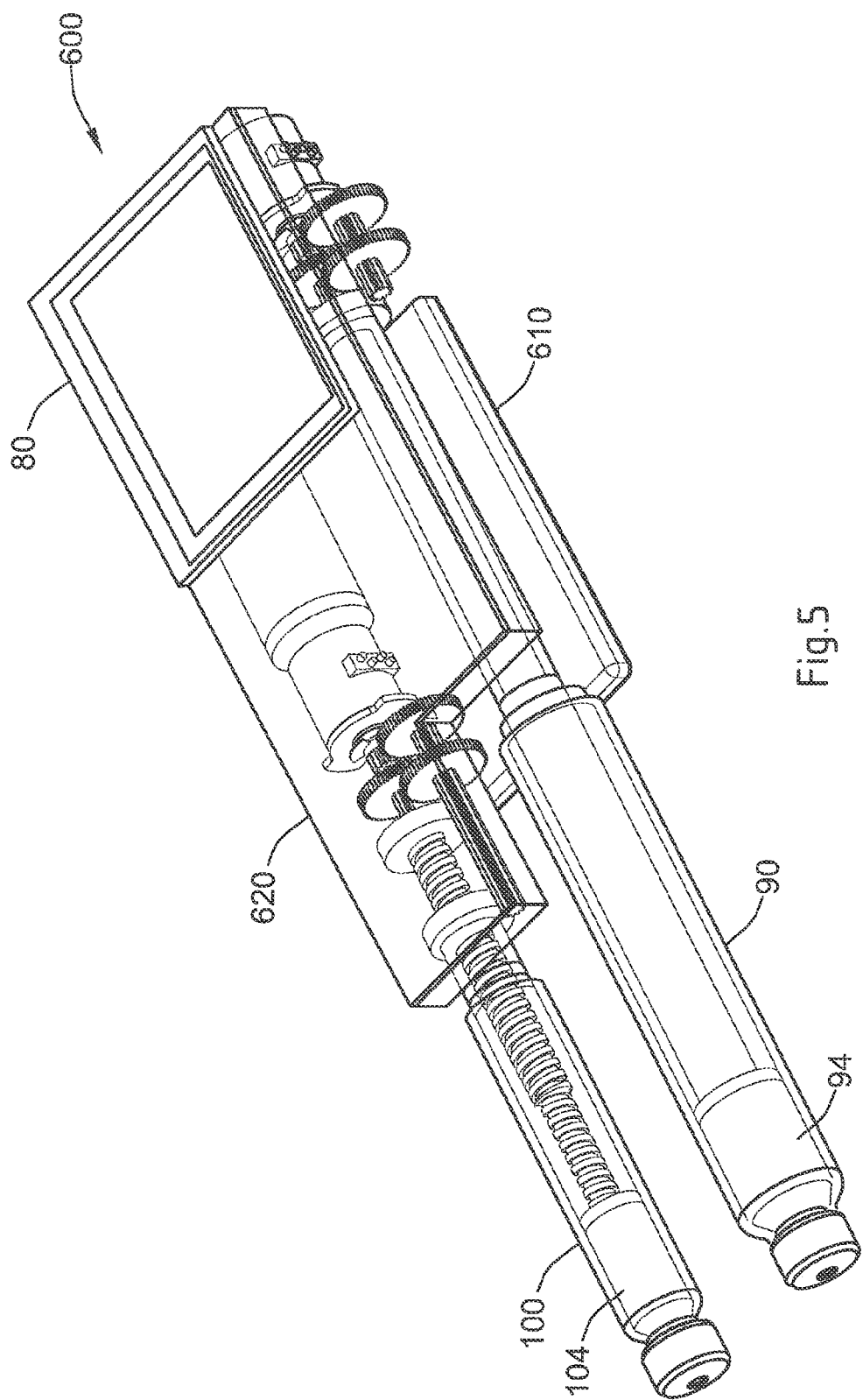

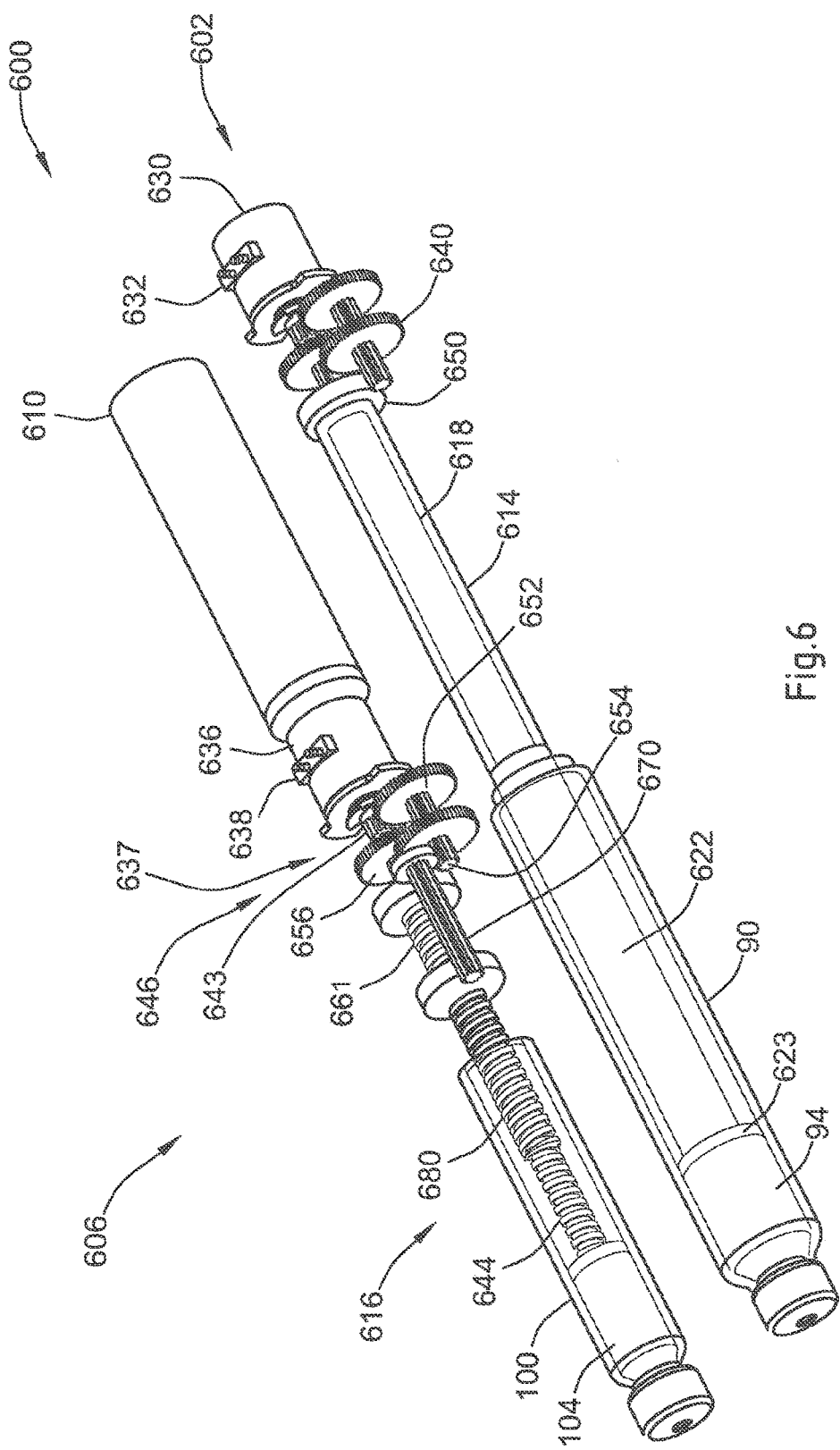

MEDICAL DEVICE FOR DELIVERING AT LEAST ONE FLUID FROM A MEDICAL DEVICE

CROSS REFERENCE TO RELATED APPLICATIONS

The present application is a U.S. National Phase Application pursuant to 35 U.S.C. §371 of International Application No. PCT/EP2012/074055 filed Nov. 30, 2012, which claims priority to European Patent Application No. 11191263.0 filed Nov. 30, 2011. The entire disclosure contents of these applications are herewith incorporated by reference into the present application.

TECHNICAL FIELD

The invention relates to a medical device and a method for delivering at least one fluid from a medical device. More particularly, the present patent application relates to medical devices for delivering at least one drug agent from a reservoir, in particular two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1, such as GLP-1, or GLP-1, analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

After an injection, independently of the number of medicaments or reservoirs, there may be the problem of leakage of medicament from the medical device, when using an electromechanical device in order to deliver a dosage. The electromechanical device in this case exerts a pressure via a gearing arrangement on a bung, which bung moves inside the reservoir and thus pushes a medicament out of the corresponding reservoir. When the delivery of the medicament is completed, the electromechanical device maintains the pressure on the fluid medicaments. Thus, after a movement of the electromechanical device a small amount of liquid will still come out of the medical device, as the bung (through which a pressure is exerted on the fluid medicament) can expand after the injection and because the friction between the bung and the cartridge containing the medicament can slightly decrease after time. Thus even without an instructed movement of the electromechanical device, a continued ejection is taking place.

Generally, this problem does not occur when using a purely mechanical actuation of the ejection, for example when a user presses the dose button. When the user releases the dose button again, the pressure is reduced preventing any further ejection of liquid from the mechanical device. However, in an electromechanical device, the motor and the gearing arrangement may maintain the pressure on the bung, as already stated above. In addition, the mechanical parts of the gearing arrangement may store some of the energy generated by the motor and release it slowly after the motor stops (similar to a tensioned spring), thus moving the bung a small further amount causing a further ejection or leakage of medicament.

In the state of the art there have been approaches to solve the problem of so called "after-dripping". For instance, the U.S. Pat. No. 6,613,019 B2, describes a method to reduce injection time and improve dose accuracy of a liquid medication delivery system. It is described, that a piston rod is moved to a position corresponding to a dose greater than the intended one. Immediately following this, the piston rod is reversed to a position corresponding to the intended dose.

For example, in case of malfunctions or canting of the piston rod or bung, a reverse movement of the piston may not be possible, which may result in administering an over dose. Additionally, as described above, the pressure on the fluid medicament is still maintained when using electromechanical devices. Thus, in case of temperature variations for example, a later expansion of the bung or the liquid would still lead to further ejections of small amounts of liquid.

Valves, which are operated by pressure, can also be provided in the flow path of the medical device to better control the ejection of fluids and to further securely prevent leakage when the pressure on the fluid is small enough or the device is shut down. Such valves, though, cannot prevent leakage of the medical device in use, since, when the pressure on the fluids is maintained by the electromechanical device during usage, the valve is kept just at the valve's closing pressure. Small variations in environmental conditions, such as temperature or air pressure, can easily cause leakage again.

In view of the aforementioned, the invention faces the technical problem of preventing after-dripping and at the same time improving the safety and the dose accuracy of a medical device.

The technical problem is solved by a method for delivering at least one fluid from a medical device, wherein the fluid is ejected from a reservoir by an advancing movement of a bung, wherein an electromechanical device is instructed to move the bung via a piston over a predetermined distance and wherein, after a dwell time following the advancing movement of the piston, the piston is retracted by the electromechanical device.

Firstly, by including a dwell time in this way to the delivery process, it is guaranteed, that there is enough time for the bung to expand and reach the desired destination. Thus the dose accuracy is improved. The desired dose is ejected from the device, without any further after-dripping of liquid, that was supposed to be injected into the patient's skin, for example. The fluid is preferably a medicament or drug agent. During the dwell time the user can be instructed to keep the injection needle of the medical device inserted into the skin. In this way, the user can be sure, to wait for the dwell time before removing the needle, for example. Since the bung is not advanced any further than the position corresponding to the desired dose to be delivered, the danger of administering an overdose is significantly reduced.

Secondly, by retracting the piston by the electromechanical device after a dwell time following the advancing movement of the piston, the pressure is removed or reduced from the fluid. Even after the dwell period, for example when a user removes the medical device, or in particular the injection needle, from the injection site, any leakage of fluids from the medical device is at least reduced or even prevented. Even later, small variations in temperature or pressure do not directly cause a leakage of the fluid, since the pressure on the fluid has been reduced by the retraction of the piston. For this purpose the piston may in particular not be fixedly attached to the element, which is in direct contact with the fluid, for example the bung, such that the piston can be retracted without creating an underpressure or negative pressure in the reservoir from which the fluid is ejected.

The meaning of the expression "bung" is to be understood in a broad sense, such that a bung can also be a stopper, a plug or a peg, for example. There also might be combinations of such element in order to transfer the force from the piston to the fluid.

Users of mechanically working insulin pens, for example, are used to wait for a certain dwell time or period, during which they keep the needle in their skin before removing the medical device. Thus, when switching from a purely mechanically driven medical device to an electromechanically driven medical device, the user does not need to adapt, since the steps for administering a drug from a medical device stays substantially the same.

It is possible to use the method according to the invention to deliver more than one fluid, in particular two fluids, from a medical device. In that case the terms fluid, reservoir, bung, electromechanical device and/or piston are understood to mean first fluid, first reservoir, first bung, first electromechanical device and/or first piston, respectively. The method according to the invention and the embodiments described herein are also applicable to the corresponding second, third or more elements.

By using an electromechanical device, a piston and a bung to transfer a force on the fluid, a more precise dose accuracy can be achieved compared to a mechanically driven device. Moreover the movement of the electromechanical device can be monitored by sensors, for example by motion detectors, providing further security and dose accuracy.

According to an embodiment of the method according to the invention, the electromechanical device is a stepper motor or a brushless DC motor. These motor types are especially advantageous, since they allow for a precise control of the mechanical movement, since they are controlled in single discrete pulses instead of a continuously driven dc motor for example, and thus permit a further improvement in dose accuracy. Further, precisely defined forward and backward movements of the motor are possible, allowing for precise advancing movements and retractions of the piston rod. Consequently, further improved security and safety of the method is achievable.

It is further advantageous, when the piston is moved by the electromechanical device via a gearing arrangement. By providing a gearing arrangement the mechanical movement of the electromechanical device via the piston to the bung can be precisely adjusted according to the necessary movement of the bung or to the required dispense speed. In this way a further improvement of the dose accuracy can be achieved by an increased precision through a different (for example higher) gear ratio, or a greater speed can be achieved, reducing the time needed to eject a certain amount of the fluid, for example.

According to another embodiment of the method, the dwell time is predetermined. By providing a predetermined dwell time, no calculations need to be done by the medical device. This is particularly advantageous, when the method is performed by a portable medical device, since only a limited amount of power can be provided for calculations by a battery, for example, before a recharging is necessary. Such a dwell time can be indicated on a display of the medical device, for example. The dwell time can also be provided to the user beforehand, such that no means for indicating the dwell time to the user on the medical device during the administration are necessary, for instance.

If the dwell time is variably adjusted, the dwell time can for example be reduced, while an after-dripping effect is still prevented. Such an adjustment can be calculated based on information about the dose ejected, for example. It is also possible to provide flow sensors, measuring the actual flow of the fluid out of the medical device and reducing or extending the dwell time accordingly.

According to another embodiment of the method, the dwell time is at least 4 seconds, in particular at least 6, seconds and preferably at least 10, seconds. By providing at least a short dwell time, dose accuracy can be maintained even if the user removes the injection needle early. This is because an after dripping effect is prevented and the complete dose of the fluid is administered to the user and is not lost to the environment because the user removed the injection needle too early, for example. Also, by providing this short dwell time, a quicker and more user-friendly dose delivery process can be provided. An increased dwell time prevents after-dripping too, and also further improves dose accuracy.

According to a next embodiment of the method according to the invention, the electromechanical device is moved with a second forward movement within the dwell time. This moves the piston with another advancing movement. This may cause a further improvement of the dose accuracy. After ejecting a certain amount of fluid, the back pressure of the fluid may cause the bung not to reach the desired position corresponding to the dose to be delivered. For example, when a telescoping piston rod is being used, which is rotated to be extended, the torque acting on the piston rod may distort or torsionally twist the piston rod or other mechanical elements in a drive train or gearing arrangement, for example. When these parts extend or relax again after the advancing movement is completed and the power to the electromechanical device is turned off in order to save power, a backward movement of the electromechanical device can be the result, if the pressure of the fluid is strong enough to prevent the movement of the bung, for example. With another or a second forward movement of the electromechanical device advancing the piston, this difference to the desired position of the bung corresponding to the desired dose delivery is compensated for.

It is in particular possible, to detect the backwards movement of the electromechanical device by means of a motion detector, for example. In this way, the exact amount of lacking advancing movement can be compensated for with the second forward movement of the electromechanical device. It is also possible though, to define a fixed distance for the second forward movement of the electromechanical device and thus the second advancing movement of the piston based on experimental or theoretical data, for example.

Alternatively, it is also possible to prevent this backward movement of the electromechanical device, by keeping the power supplied to the electromechanical device. This maintains enough torque or force to the electromechanical device to prevent any backward movements and thus the bung eventually reaches the desired position without another advancing movement.

Preferably, after said advancing movement of the piston, the electromechanical device is turned off, a backward movement of the electromechanical device is detected while the electromechanical device is turned off and the second forward movement is determined from the detected backward movement. The power consumption of the device is decreased in this way.

After the other or second advancing movement the piston is retracted. The dosing accuracy can be further increased in this way, while at the same time the power consumption is kept at a minimum.

It is advantageous to wait for a time period, after the advancing movement of the piston, before the second forward movement of the electromechanical during the dwell time is performed, for example at least 1 second. The second forward movement thus does not directly follow the advancing movement. Likewise, it is advantageous to wait for a certain time period, after the second forward movement before the piston is retracted. These waiting intervals account for the relaxation effects, such as bung expansion, that give rise to after-dripping and imprecise dosing.

According to another embodiment of the method, the advancing movement of the piston accounts for a previous retraction of the piston. When the piston is retracted after a dose delivery in order to release the pressure on the fluid and to prevent after dripping, during a subsequent dose delivery the refracted movement is compensated for at the beginning of a subsequent dose delivery. Consequently, the dose accuracy of the next dose delivery is not negatively affected by the retraction.

It is further preferred, when a second fluid is ejected from a second reservoir by an advancing movement of a second bung, the same or another electromechanical device is instructed to move the second bung via a second piston over a predetermined distance and, after a dwell time following the advancing movement of the second piston, the first piston and the second piston are retracted by the respective electromechanical device.

In this case, the aforementioned fluid, reservoir, bung and piston are considered as the first corresponding elements. In such an embodiment with two fluids, the two fluids are ejected from two reservoirs into separate fluid pathways and the fluid pathways are combined in a dispense interface, for example. The fluid pathways can each have a valve to better control the ejection of the fluids. Eventually, the fluids are dispensed through a single outlet. Because during the dwell time the pistons are not yet retracted, the pressure kept up in each fluid minimizes the risk, that there is a cross contamination between the fluids and also increases the dose accuracy. The dwell time can be understood as a common dwell time for both ejections, starting after the advancing movement of either the first or the second piston. There can also be a separate dwell time for each piston or fluid. Thus it is especially advantageous, when the pistons are only retracted after each piston has advanced with another movement. The aforementioned embodiments and advantages described herein with respect to a method for delivering one fluid are likewise applicable to corresponding embodiments for delivering a second, third or even more fluids. For example, each piston can be moved via a gearing arrangement each by an electromechanical device such as a stepper motor or a brushless DC motor.

It is further preferred, that the second piston is moved after the advancing movement of the first piston. In this way, the ejection can be better controlled. In the device with two fluids and two flow paths, a valve may be provided in each flow path. The valves may be arranged in such a way that back flow into the cartridges is prevented. For example, only one valve is opened at a time, and the fluid flows inside the device are more predictable compared to when more than one fluid is ejected at a time. Thus, cross contamination can be prevented and more accurate predictions of doses can be done.

It is especially preferred, that each piston is driven by a separate electromechanical device, although a single electromechanical device is also possible that connects to each piston through a switching gearing arrangement. When individual and independent electromechanical devices are provided for each piston or fluid, there is no need for any switching mechanisms, and each electromechanical device is able to control one piston individually.

In case the first piston and the second piston are moved, for example advanced and/or retracted, one after another, it is sufficient to provide less powerful power sources to the medical device, since the pistons are not moved at the same time, which might double the power consumption for the time of movement. It is of course possible to change the order of moving the pistons.

It is in particular preferred, when the second piston is moved within the dwell time with another advancing movement. This causes a further improvement of the dose accuracy for the second fluid, as well. As explained in connection with a first bung, with another or a second advancing movement of the second piston, the difference of the actual position to the desired position of the second bung corresponding to the desired dose delivery is compensated for.

It is in particular possible, to detect the backward movement of a second electromechanical device by means of a second motion detector, for example. Such backward movement can result, for example, when a telescoping piston rod is used, which is rotated to be extended, the torque acting on the piston rod may distort or torsionally twist the piston rod or other mechanical elements in a drive train or gearing arrangement, for example. When these parts extend or relax again after the advancing movement is completed and the power to the electromechanical device is turned off in order to save power, a backward movement of the electromechanical device can be the result. The exact amount of lacking advancing movement detected by the motion detector can be compensated for with the other or second advancing movement. After the other advancing movement the second piston is retracted.

Thus, for a method delivering two fluids, there would preferably first be the advancing movement of the first piston, afterwards the advancing movement of the second piston. During the dwell time, the power may be turned off at both electromechanical devices, which might result in a slight backwards movement of the electromechanical devices. The electromechanical devices may not only be turned off during the dwell time, but also while the respective other electromechanical device is used or moved. The movements are detected by separate motion detectors. Then, there is the other advancing movement of the first piston and afterwards the other advancing movement of the second piston to correct the detected backwards movements, or the other way around. After that, there is preferably the retraction of the first piston and afterwards the refraction of the second piston, or the other way around.

The technical problem is also solved by a medical device, in particular for performing a method according to the invention, comprising a reservoir, a bung, a piston, an electromechanical device and a control unit. The reservoir, the bung, the piston and the electromechanical device controlled by the control unit are arranged such that the electromechanical device can be instructed to move the bung via a piston over a predetermined distance and a fluid is ejected from the reservoir by an advancing movement of the bung. Furthermore, the control unit is configured such that, after a dwell time following the advancing movement of the piston, the piston is retracted by the electromechanical device.

On the one hand, by configuring the control unit such that, a dwell time is provided, it is guaranteed, that there is enough time for the bung substantially to expand and reach the desired destination. Thus the dose accuracy may be improved. On the other hand, by configuring the control unit such that the piston is retractable by the electromechanical device after a dwell time following the advancing movement of the piston, the pressure is taken away or released from the fluid. Even after the dwell period, for example when a user removes the medical device, or in particular the injection needle, from the injection site, any leakage of fluids from the medical device is at least reduced or even prevented.

If the medical device further comprises a gearing arrangement arranged such that the bung is moved by the electromechanical device by the gearing arrangement, a desired precision can be adjusted by the design of the gearing arrangement. The transmission of the mechanical movement of the electromechanical device to the bung can be adjusted according to the desired precision, for example. The speed of the movement of the bung and the force exerted by the bung on the fluid needed to eject the fluid are also controllable.

A further improvement of the dose accuracy can be achieved, when the control unit is configured such that, within the dwell time, the electromechanical device is moved with a second forward movement. This moves the piston with another advancing movement, in order to compensate the difference of the actual position to the desired position of the bung corresponding to the desired dose delivery.

It is in particular possible, to provide a motion detector, for example an optical encoder detecting the rotation of the electromechanical device by an alternating interruption of a light source. The exact amount of lacking advancing movement detected by the motion detector can then be compensated for with the another advancing movement. After the another advancing movement the piston is retracted.

In an example embodiment, the medical device further comprises a second reservoir, a second bung and a second piston, wherein the second reservoir, the second bung, the second piston and the electromechanical device controlled by the control unit are arranged such that the electromechanical device can be instructed to move the second bung via a second piston over a predetermined distance and a second fluid may be ejected from the second reservoir by an advancing movement of the second bung. The control unit may be configured such that, after a dwell time following the advancing movement of the second piston, the first piston and the second piston is retracted by the electromechanical device. Because during the dwell time the pistons are not yet retracted, the pressure kept up in each fluid minimizes the risk that there is a cross contamination between the fluids and thus increases the dose accuracy. The aforementioned embodiments and advantages described herein with respect to a method for delivering one or two fluids and with respect to a medical device are likewise applicable to corresponding embodiments of the medical device for delivering a second, third or even more fluids. For example, there can be individual control units for each of multiple electromechanical devices, or there can also be a common control unit.

In another example embodiment, the control unit is configured such that the second piston is moved after the advancing movement of the first piston. This way a better dose accuracy can be achieved, since the ejection can be better controlled. It is also sufficient to provide less powerful power sources to the medical device, since the pistons are not moved at the same time, which might double the power consumption for the time of movement.

When the electromechanical device and/or the control unit are configured such that the first piston and the second piston are not simultaneously moved, the further improvement of safety can be achieved, since it can be excluded by software or even hardware, that the pistons are simultaneously moved, minimizing the risk of intermixing the fluids or overloading or overburdening the battery, for example.

The medical device or drug delivery device may be a portable medical device. Reliably increasing the dose accuracy for portable devices is especially desired, since due to transportation and movements of the device the accuracy can easily be impaired. Further, drug doses need to be as precise as possible since over- and/or underdoses can have harmful consequences for the user. Furthermore, there is only limited space and power available in portable device, especially qualifying the method and the medical device according to the invention for use in portable devices and/or drug delivery devices.

BRIEF DESCRIPTION OF THE FIGURES

These as well as other advantages of various aspects of the method and the medical device according to the present invention will become apparent to those of ordinary skill in the art by reading the following detailed description, with appropriate reference to the accompanying drawing, in which:

FIGS. 4a and 4b illustrates a motion detection system that may be used with the drive mechanism illustrated in FIG. 2;

FIG. 5 illustrates a schematic view of an alternative drive mechanism for use with the drug delivery device;

FIG. 6 illustrates a schematic view of the alternative drive mechanism illustrated in FIG. 5 with certain elements removed;

DETAILED DESCRIPTION

Figure 1:
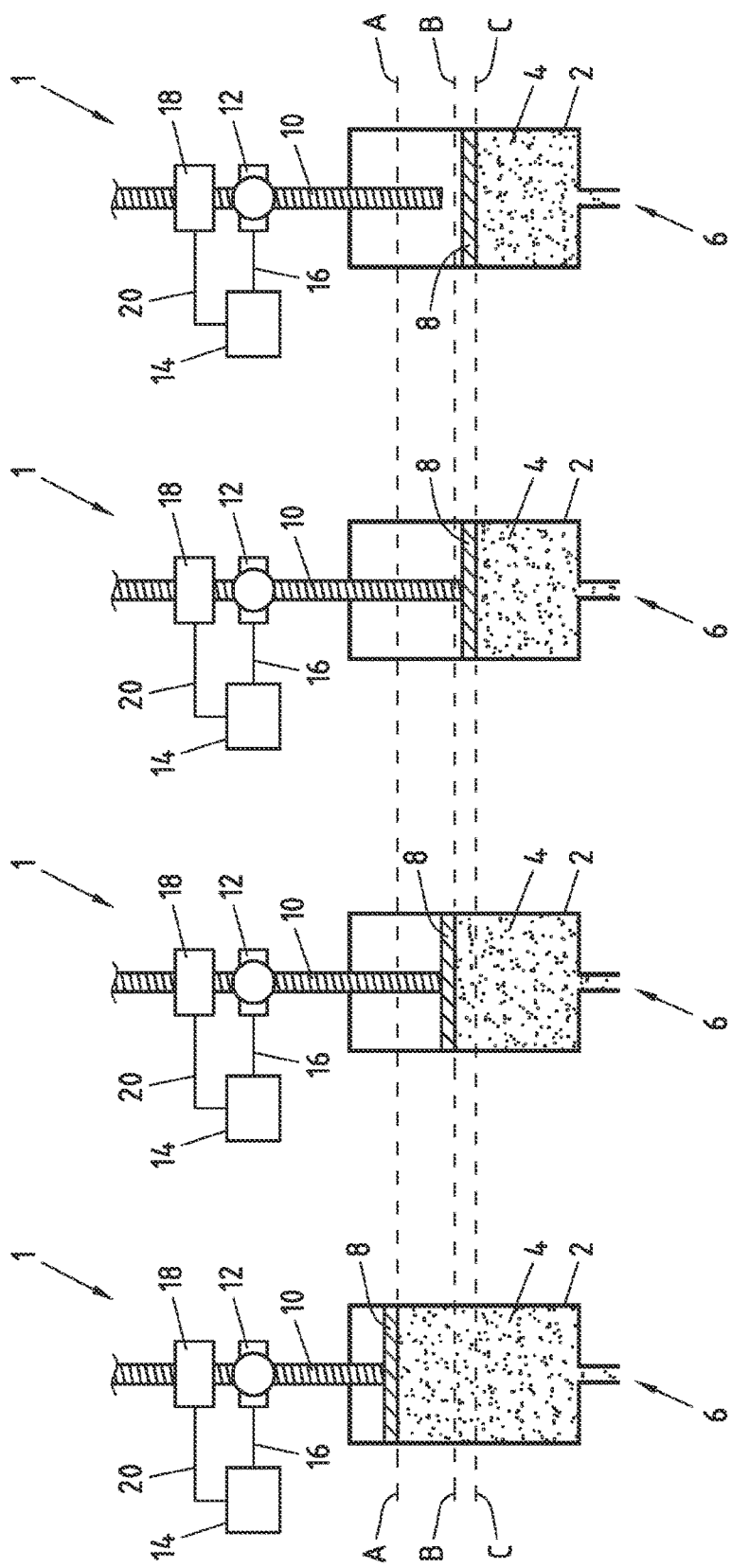
FIGS. 1a-1d illustrate schematic views of different states of an exemplary embodiment of the method according to the invention performed by an exemplary embodiment of the medical device according to the invention.

FIG. 1a-1d illustrate a schematic view of different states of an exemplary embodiment of the method according to the invention performed by an exemplary embodiment of the medical device according to the invention. The medical device 1 comprises a reservoir 2 containing a fluid 4 in form of a medicament or drug agent 4. The reservoir has an outlet 6, through which the fluid 4 can be ejected. To increase the pressure in the fluid 4 and thus guide the fluid 4 out of the reservoir 2, a bung 8 can exert a pressure on the fluid 4. The bung 8 is in contact with a piston 10, which is able to transfer the movement of an electromechanical device 12 in form of a motor onto the bung 8. Of course, there can also be provided gearing arrangements or piston rods as exemplarily described in FIG. 5. The motor 12 is controlled by a control unit 14 over the connection 16. The control unit 14 can be a microprocessor or a dedicated motor driver, for example. The control unit gets feedback with respect to the actual movement of the motor 12 from a motion detector 18 via the connection 20. Even though, the motion detector 18 is illustrated as a separate unit, the motion detector can also be directly integrated in the housing of the motor 12, for example. The motion detector 18 detects the motion of the motor 12 directly, not the motion of the lead screw, although detection of the motion of the lead screw remains another possible arrangement.

In FIG. 1a, the bung 8 is in position A, as illustrated by the topmost vertical line. By instruction of the control unit 14, which may be received from a memory, another control unit or a user interface, the motor 12 drives the piston 10 against the bung 8, such that the bung moves towards the opening 6 and the fluid 4 is partially ejected form the reservoir 2 through the opening 6.

At the same time the movement of the motor 12, for example of the pinion of the motor 12 can be monitored by the motion detector 18.

The state after the advancing movement of the bung 8 is illustrated in FIG. 1b. The bung 8 is now in position B. Before the retraction of the bung 8 there is now the dwell time, during which the system can approach an equilibrium state. The dwell time can be 10, seconds for example. During this time the bung can expand, in case it was compressed during the forward movement, for example.

It might happen though, that the desired position of the bung 8 corresponding to a desired dose would be position C, as illustrated by the bottommost line in FIG. 1. Even though the motor 12 drove the piston 10 far enough, the bung 8 may not reach the desired position C. Due to the fact, that a part of the energy can be transformed into a reversible torsional twist of a rotating piston 10, for example, the bung 8 does not reach the desired position C, but only reaches position B. There might also be other points and/or causes between motor 12 and bung 8, where and why energy might not be transferred completely into an advancing movement of the bung 8, for example stored energy in the gearing arrangement.

This state is also illustrated in FIG. 1b. The bung is in position B and the there would only be administered a too low dosage. When the motor 12 is switched off, the energy stored in the piston rod causes the piston rod 10 to unwind (untwist), and this energy is transformed into a backwards movement of the motor 12 instead of an advancing movement of the bung 8. This backward movement of the motor 12 is detected and encoded by the motion detector 18 and is then transmitted to the control unit 14, for example.

The control unit 14 then instructs the motor 12 to advance the piston 10 and thus the bung 8 again, making up for the detected backwards movement of the motor 12. It is also possible to provide another advancing movement during the dwell time, without feedback of a motion detector 18. The amount of the other advancing movement can then be based on empirical data, for example. The other advancing movement is only optional, though it may increase dose accuracy.

As illustrated in FIG. 1c, after this other advancing movement of the bung 8, which can take place for example 1 second after the completion of the first advancing movement, the bung 8 is now in position C. If the piston 10 is left in that position after the dose is completed, there will be the problem that due to small temperature or pressure variations, the medical device 1 is prone to further leakage, since the piston 10 may impede a movement of the bung 8 upwards, thus causing leakage, when the fluid expands.

Thus, as illustrated in FIG. 1d, the piston 10 is retracted to a position backed down compared to the position of the bung 8. In this case the piston 10 is not in direct contact with the bung 8 anymore. It is also possible to keep bung 8 and piston 10 attached to each other and also retract the bung 8. In this way, fluid can be retracted from the outlet 6 such that leakage is prevented.

During a further delivery, the amount of retraction of the piston 10 or the piston 10 and the bung 8 is accounted for and compensated for, for example by advancing the bung an additional amount that is equal to the amount of the retraction.

In the following figures components of a drug delivery device for the delivery of two drugs are described. The described features are especially advantageous in combination with a method and a medical device according to the invention and the corresponding embodiments.

Figure 2:
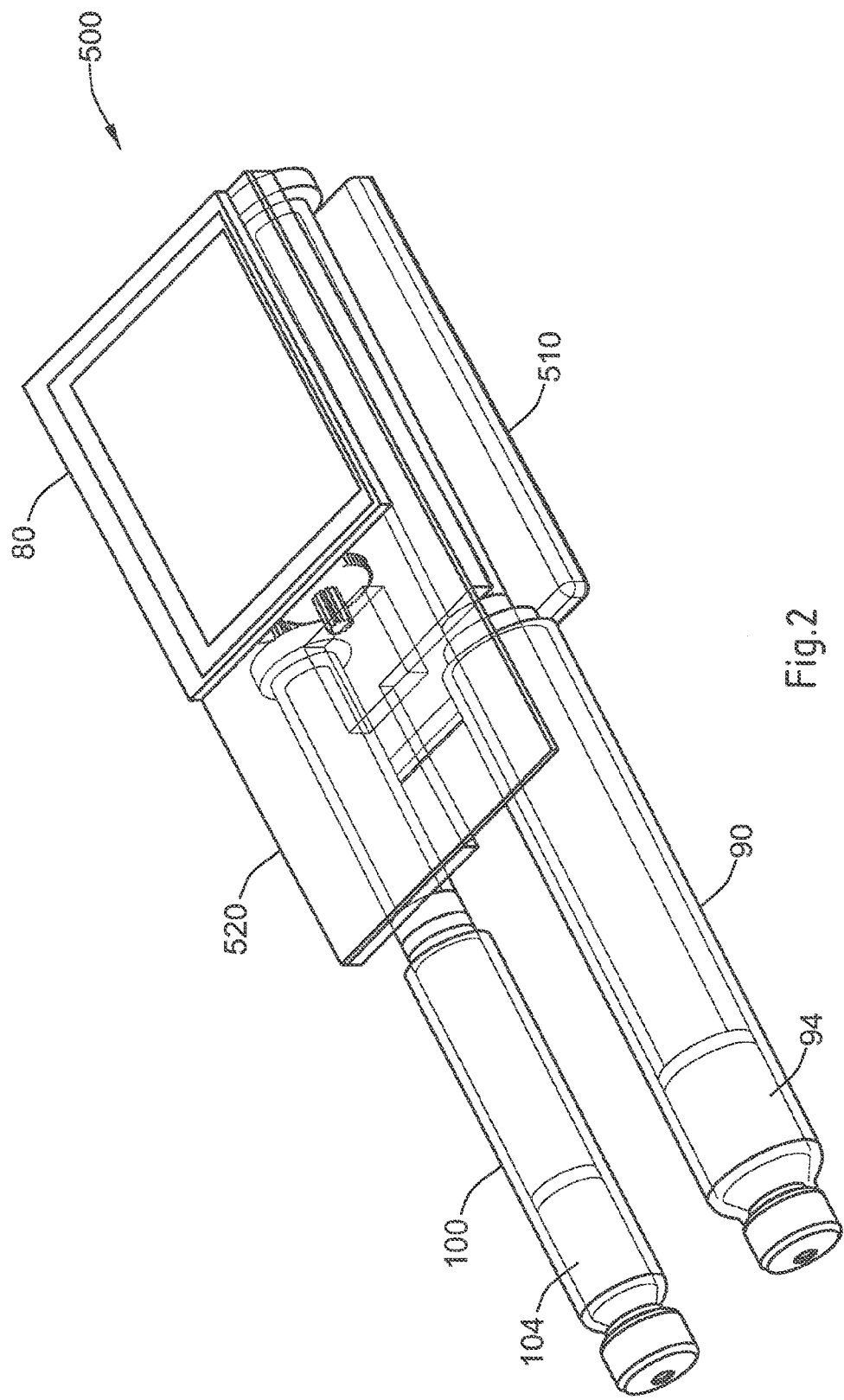
FIG. 2 illustrates a schematic view of a drive mechanism for use with the drug delivery device.

FIG. 2 illustrates various internal components of the drug delivery device 1 illustrated in FIG. 1a-1d including one preferred arrangement of an electro-mechanical system 500. FIG. 2 also illustrates a digital display 80, a printed circuit board assembly (PCBA) 520, along with a power source or battery 510. The PCBA 520 may be positioned between the digital display 80 and an electro-mechanical system 500 with the battery or power source 510 positioned beneath this electro-mechanical system. The battery or power source 510 is electronically connected to provide power to electronic components of the medical device, such as the digital display 80, the PCBA 520 and the electro-mechanical system 500. As illustrated, both the first and second reservoirs in form of cartridges 90, 100 are shown in an expended state. That is, the first and second cartridges are illustrated in an empty state having a bung at a most distal position. For example, the first cartridge 90 (which ordinarily contains the first medicament) is illustrated as having its bung 94 in the distal position. The bung 104 of the second cartridge 100 (ordinarily containing the second medicament) is illustrated in a similar position.

With reference to FIG. 2, it may be seen that there is provided a first region defining a suitable location for a power source 510 such as a replaceable battery or batteries. The power source 510 may comprise a rechargeable power source and may be recharged while the power source 510 remains in the device. Alternatively, the power source 510 may be removed from the drug delivery device 10 and recharged externally, for example, by way of a remote battery charger. This power source may comprise a Lithium-Ion or Lithium-polymer power source. In this preferred arrangement, the battery 510 comprises a generally flat and rectangular shaped power source.

Figure 3:
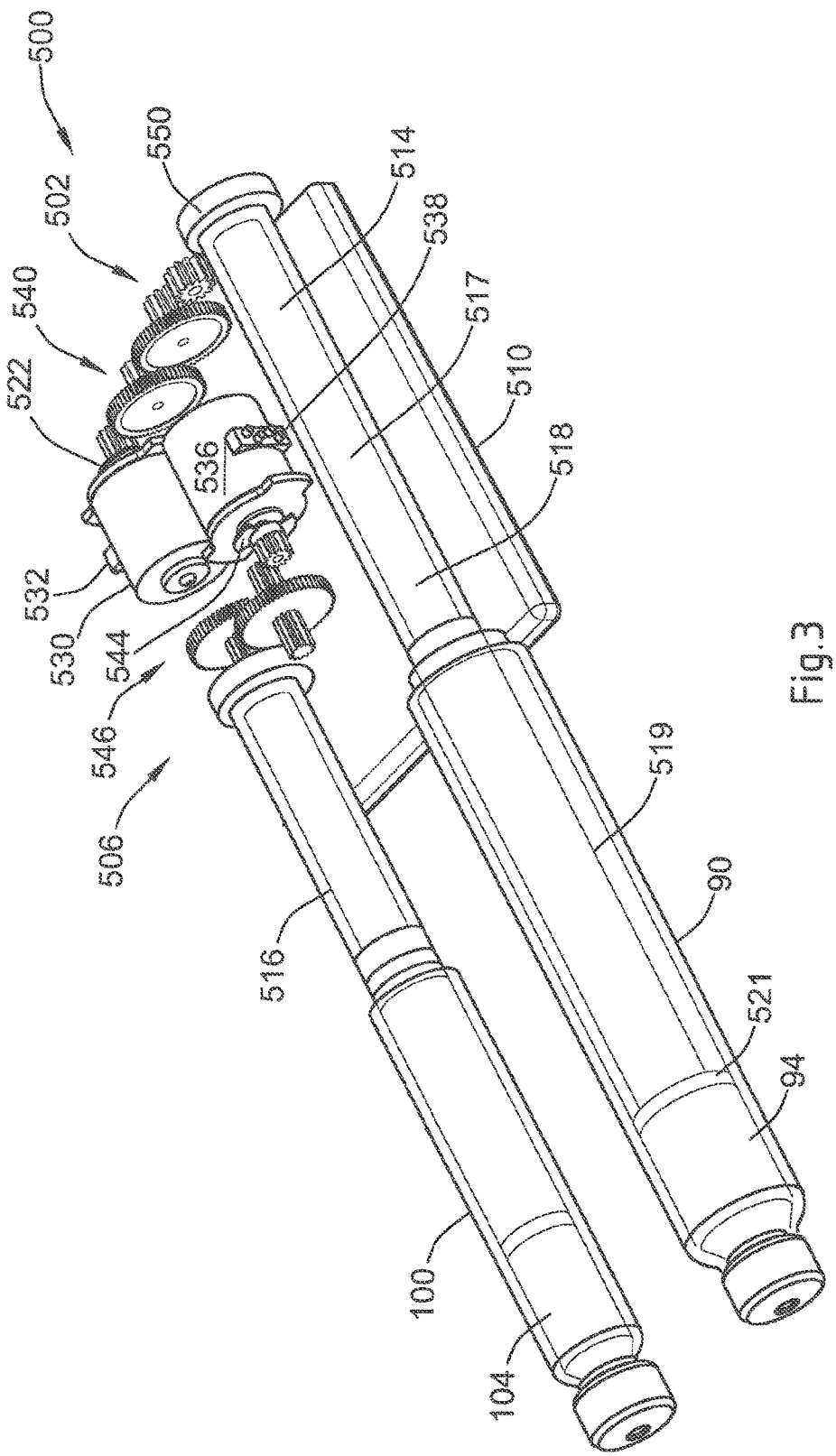
FIG. 3 illustrates another schematic view of the drive mechanism illustrated in FIG. 2.

FIG. 3 illustrates the first arrangement of the electro-mechanical system illustrated in FIG. 2 with both the digital display 80 and the PCBA 520 omitted. As illustrated in FIG. 3, the electro-mechanical system 500 operates to expel a dose from the first cartridge 90 containing the primary medicament and the second cartridge 100 containing the secondary medicament. As illustrated in FIG. 3, the first and second cartridges 90, 100 are illustrated in an empty state having bungs at a most distal position.

In this electro-mechanical system 500, the system comprises an independent mechanical driver for each cartridge 90, 100. That is, an independent mechanical driver 502 operates to expel a dose from the first cartridge 90 and an independent mechanical driver 506 operates to expel a dose from the second cartridge 100. In an alternative electro-mechanical system operating on three different medicaments, three independent mechanical drivers could be provided. The independent mechanical drivers act under control of motor drivers or of the control unit 14, for example.

The first independent mechanical driver 502 operates to expel a dose from the first cartridge 90. This first driver 502 comprises a first motor 530 that is operatively coupled to a first gearing arrangement 540. To energize this motor 530, a connector 532 is provided as a means of electrically connecting to a motor driver(not shown). This first gearing arrangement 540 is mechanically linked to a proximal portion of the first telescoping piston rod 514. The first telescoping piston rod 514 is illustrated in a fully extended position having a distal end 521 acting on the bung 94 of the first cartridge 90.

As this gearing arrangement 540 is driven by the output shaft of the first motor 530, this arrangement 540 rotates the proximal portion 518 of the first telescoping piston rod 514. As this proximal portion 518 of the piston rod 514 is rotated, the second or distal portion 519 of the piston rod 514 is driven in a distal direction.

Preferably, the proximal portion 518 of the telescope piston rod 514 comprises an external thread 517. This thread 517 engages the distal portion 519 which has an integrated nut comprising a short threaded section at a proximal end of the distal portion 519. This distal portion 519 is prevented from rotating via a key acting in a keyway. For example, the distal portion 519 may have one or more splines on the outside that prevent rotation. Therefore, when the first gearbox arrangement 540 causes rotation of the proximal section 518, rotation of the proximal portion 518 acts upon the distal end 521 to thereby drive the distal portion of telescope piston rod to extend along the longitudinal axis.

Moving in this distal direction, the distal end 521 of the second portion 519 of the piston rod 514 exerts a force on a bung 94 contained within the first cartridge 90. With this distal end 521 of the piston rod 514 exerting a force on the bung, the user selected dose of the first medicament is forced out of the cartridge 90 and into an attached dispense interface (not shown) and consequently out an attached needle assembly (not shown), for example.

A similar injection operation occurs with the second independent driver 506 when the controller first determines that a dose of the second medicament is called for and determines the amount of this dose. This second independent driver 506 comprises a second motor 536 that is operatively coupled to a second gearing arrangement 546. To energize this second motor 536, a connector 538 is provided as a means of electrically connecting to a motor driver (not shown). This second gearing arrangement 546 is mechanically linked to a proximal portion of a second telescoping rod 516. As previously mentioned, in certain circumstances, the controller may determine that a dose of the second medicament may not be called for and therefore this second dose would be "set" to a "0" dose.

Preferably, motors 530, 536 comprise motors suitable for electronic commutation. Most preferably, such motors may comprise either a stepper motor or a brushless DC motor.

To inject a dose of the primary and secondary medicaments, a user will first select a dose of the primary medicament by way of the human interface components on the display 80. After a dose of the drug from the primary medicament has been selected, the microcontroller will utilize a previously stored algorithm for determining the dose size of a second drug from a second medicament cartridge. This pre-defined algorithm may help to determine at least in part the dose of the second medicament, for example based on a pre-selected therapeutic profile. In one arrangement, these therapeutic profiles are user selectable. Alternatively, these therapeutic profiles may be password protected and selectable only by a person authorized with the password, such a physician or health care professional. In yet another arrangement, the therapeutic profile may only be set by the manufacturer or the supplier of the drug delivery device. As such, the drug delivery device may be provided with only one profile.

When the dose sizes of the first and second medicaments have been established, the user can press an injection button. By pressing this button, the motor drivers energize the first and the second motors 530, 536 to perform the injection process described above.

In one arrangement, both the first and second motors 530, 536 operate simultaneously so as to dispense the user selected dose of the first medicament and the subsequently calculated dose of the second medicament simultaneously. That is, both the first and the second independent mechanical drivers 502, 506 are capable of driving the respective piston rods 514, 516 at the same time. In this manner the first medicament enters a holding chamber of a dispense interface (not shown) at essentially the same time as the second medicament. One advantage of such an injecting step is that a certain degree of mixing can occur between the first and second medicament prior to actual dose administration.

In a preferred alternative arrangement, the controller may be programmed so that the first and the second independent mechanical drivers 502, 506 may be operated to dispense either the first medicament or the second medicament prior to the other medicament. Thereafter, the second or the primary medicament may then be dispensed. In one preferred arrangement, the secondary medicament is dispensed before the primary medicament.

Preferably, the first and second motors 530, 536 comprise electronic commutation. Such commutation may help to minimise the risk of a motor runaway condition. Such a motor runaway condition could occur with a system comprising a standard brushed motor experiencing a fault. In one embodiment of the motor drive system, a watchdog system may be provided. Such a system has the ability to remove power to either or both of the motors in the event of a software malfunction or a failure of the electronic hardware.

To prevent the power from being removed, the correct input from a number of sections of the electronic hardware and/or the microcontroller software will need to be provided. If one of these input parameters is incorrect, power may be removed from the motor.

In addition, preferably both motors 530, 536 may be operated in a reverse direction. This feature may be required in order to allow the piston rods 514, 516 to be moved between a first and a second position.

Preferably, the first independent mechanical driver 502 illustrated in FIG. 3 comprises a first motion detection system 522. FIG. 4*a* illustrates a perspective view of the first motor 530 illustrated in FIG. 3. FIG. 4*b* illustrates a preferred motion detection system 522 comprising the first motor 530 illustrated in FIG. 4*a* in conjunction with a digital encoder 534.

As illustrated in FIGS. 4*a* and 4*b*, such a motion detection system 522 may be beneficial as it can be utilized to provide operational and positional and/or directional feedback from the first independent driver 502 to the control unit of the drug delivery device. For example, with respect to the first independent driver 502, a preferred motion detection system 522 may be achieved through the use of a first motor pinion 524. This first pinion 524 is operatively coupled to an output shaft 531 of the first motor 530. The first pinion 524 comprises a rotating gearing portion 526 that drives a first gear of the first gearing arrangement 540 (see, e.g., FIG. 3). The first motor pinion 524 also comprises a plurality of flags 528*a-b*. In this first motion detection system arrangement 522, the first pinion 524 comprises a first flag 528*a* and a second flag 528*b*. These two flags 528*a-b* are positioned on the motor pinion 524 so that they pass through a first optical encoder 534 as the motor output shaft 531 and hence the connected first pinion 524 rotate when the motor is driven.

Preferably, as the first and second flags 528*a-b* pass through the first optical encoder 534, the encoder 534 can send certain electrical pulses to the microcontroller. The optical encoder 534 sends two electrical pulses per motor output shaft revolution to the microcontroller. As such, the microcontroller can therefore monitor motor output shaft rotation. This may be advantageous to detect position errors or events that could occur during a dose administration step such as jamming of the electro-mechanical system, incorrect mounting of a dispense interface or needle assembly, or where there is a blocked needle.

In another embodiment, the first pinion 524 comprises a plurality of flags 528*a-b*, for example 3 or 4 flags or even more. In a further embodiment, the optical encoder 534 comprises two optical paths which are interrupted by flags 528*a-b*. This may be achieved by a single light source and two optical detectors next to each other, so that they are shaded by the flags 528*a-b* one after the other when the pinion 524 rotates. In this way, the direction of rotation can be detected.

Preferably, the first pinion 524 comprises a plastic injection molded pinion. Such a plastic injection molded part may be attached to the output motor shaft 531. The optical encoder 534 may be located and attached to a gearbox housing. Such a housing may contain both the first gearing arrangement 540 along with the optical encoder 534. The encoder 534 is preferably in electrical communication with the control unit potentially via a flexible portion of the PCBA. In a preferred arrangement, the second independent mechanical driver 506 illustrated in FIGS. 2 and 3 comprises a second motion detection system 544 that operates in a similar fashion as the first motion detection system 522 of the first mechanical driver 502.

The number of flags and the number of detectors can be increased in order to increase the accuracy of the motion detector. Preferably five flags are provided with two detectors for a motion detector resulting in 20 signals per single revolution of the pinion.

FIG. 5 illustrates various internal components of the drug delivery device including a preferred alternative electro-mechanical system 600. FIG. 5 illustrates the digital display 80, a printed circuit board assembly (PCBA) 620, along with a power source or battery 610. The PCBA 620 may be positioned between the digital display 80 and an electro-mechanical system 600 with the battery or power source 610 positioned beneath this electro-mechanical system. The battery or power source 610 is electronically connected to provide power to the digital display 80, the PCBA 620 and the electro-mechanical system 600. The digital display 80 and the PCBA 620 of this alternative electro-mechanical system 600 operate in a similar manner as previously described.

As illustrated, both the first and second cartridges 90, 100 are shown in an expended state. That is, the first and second cartridges are illustrated in an empty state having a bung at a most distal position. For example, the first cartridge 90 (containing the first medicament) is illustrated as having its bung 94 at the end or most distal position. The bung 104 of the second cartridge 100 (containing the second medicament) is illustrated in a similar end position.

FIG. 6 illustrates the electro-mechanical system illustrated in FIG. 5 with both the digital display 80 and the PCBA 620 omitted. As illustrated, this alternative electro-mechanical system 600 operates to expel a dose from the first cartridge 90 containing a primary medicament and the second cartridge 100 containing a secondary medicament. In this preferred electro-mechanical system 600, the system comprises an independent mechanical driver for both the first cartridge and the second cartridge. That is, an independent mechanical driver 602 operates to expel a dose from the first cartridge 90, and an independent mechanical driver 606 operates to expel a dose from the second cartridge 100. If this preferred electro-mechanical system 600 were to be reconfigured to operate on three different medicaments contained within three separate cartridges, three independent mechanical drivers could be provided so as to administer a combined dose. The independent mechanical drivers act under control of the control unit 14, for example by motor drivers controlled by the control unit 14.

The first independent mechanical driver 602 operates to expel a dose from the first cartridge 90 and operates in a similar manner as the independent drivers 502, 506 described with reference to the electro-mechanical system 500 illustrated in FIGS. 2 and 3 above. That is, this first independent driver 602 comprises a first motor 630 that is operatively coupled to a first gearing arrangement 640. To energize this motor 630, a connector 632 is provided as a means of electrically connecting to a motor driver (not shown). This first gearing arrangement 640 is mechanically linked to a proximal portion of the telescoping piston rod 614. As this gearing arrangement 640 is driven by an output shaft of the first motor 632, this arrangement 640 rotates the proximal portion 618 of the telescoping piston rod 614. As this proximal portion 618 of the piston rod 614 is rotated, the second or distal portion 622 of the piston rod 614 is driven in a distal direction. Moving in this distal direction, a distal end 623 of the second portion 622 of the piston rod 614 exerts a force on the bung 94 contained within the first cartridge 90. With a distal end 623 of the piston rod 614 exerting a force on the bung 94, the user selected dose amount of the first medicament is forced out of the cartridge 90 and into an attached dispense interface (not shown) and consequently out an attached needle assembly (not shown) as previously discussed.

The second independent mechanical driver 606 operates to expel a dose from the second cartridge 100 in a different manner than the first independent driver 602. That is, this second mechanical driver 606 comprises a second motor 636 that is operatively coupled to a second gearing arrangement 646. To energize this motor 636, a connector 638 is provided as a means of electrically connecting to the motor driver 334.

This independent mechanical driver 606 further comprises a telescope piston rod 616. The second gearing arrangement 646 is mechanically linked to a proximal portion 661 of the telescoping piston rod 616. As this gearing arrangement 646 is driven by the output shaft of the second motor 636, this arrangement 646 rotates the proximal portion 661 of the telescoping piston rod 616.

The second gearing arrangement 646 comprises a motor pinion along with a plurality of compound gears (here four compound gears) along with a telescope input piston rod. At least one of the compound gears is elongated to enable continuous mesh engagement with the input piston rod as the telescope extends in a distal direction to exert an axially pressure on the cartridge bung 104 so as to expel a dose from the cartridge. The elongated gear may be referred to as a transfer shaft. The gearbox arrangement preferably has a ratio of 124:1. That is, for every revolution of the telescope input screw the output shaft of the second motor rotates 124 times. In the illustrated second gearing arrangement 646, this gearing arrangement 646 is created by way of five stages. As those skilled in the art will recognize, alternative gearing arrangements may also be used.

The second gearing arrangement 646 comprises three compound reduction gears 652, 654, and 656. These three compound reduction gears may be mounted on two parallel stainless steel pins. The remaining stages may be mounted on molded plastic bearing features. A motor pinion 643 is provided on an output shaft of the second motor 636 and is retained on this shaft 637, preferably by way of an interference or friction fit connection.

As described above, the motor pinion 643 may be provided with two or more mounted "flag" features that interrupt the motion detect optical sensor. The flags are symmetrically spaced around the cylindrical axis of the pinion.

Figure 7:
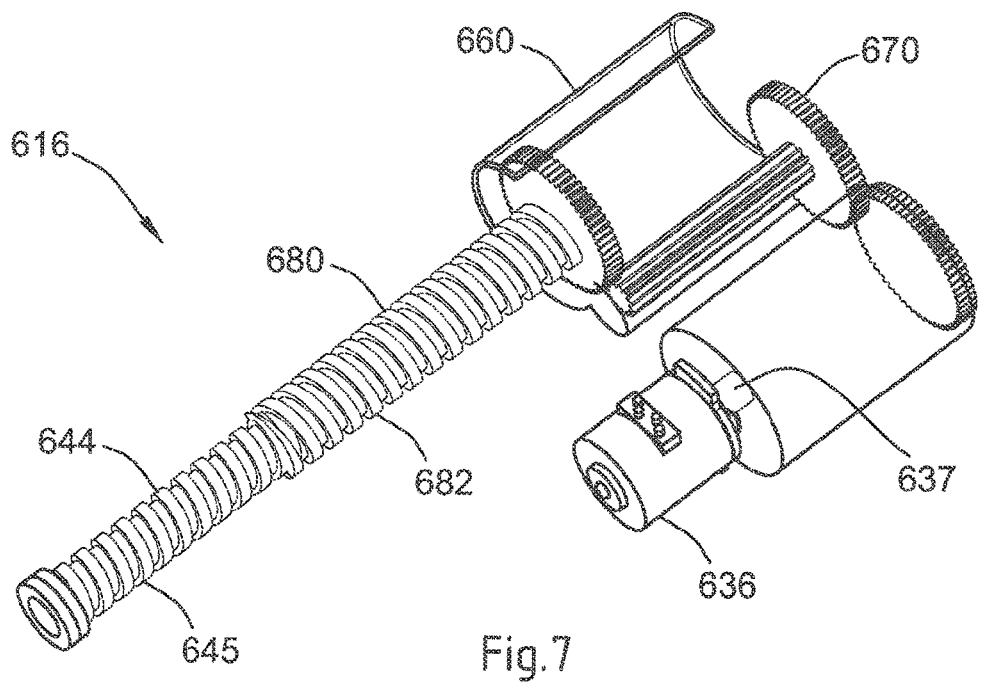
FIG. 7 illustrates a schematic view of a telescope piston rod and gearing arrangement illustrated in FIG. 6.
Figure 8:
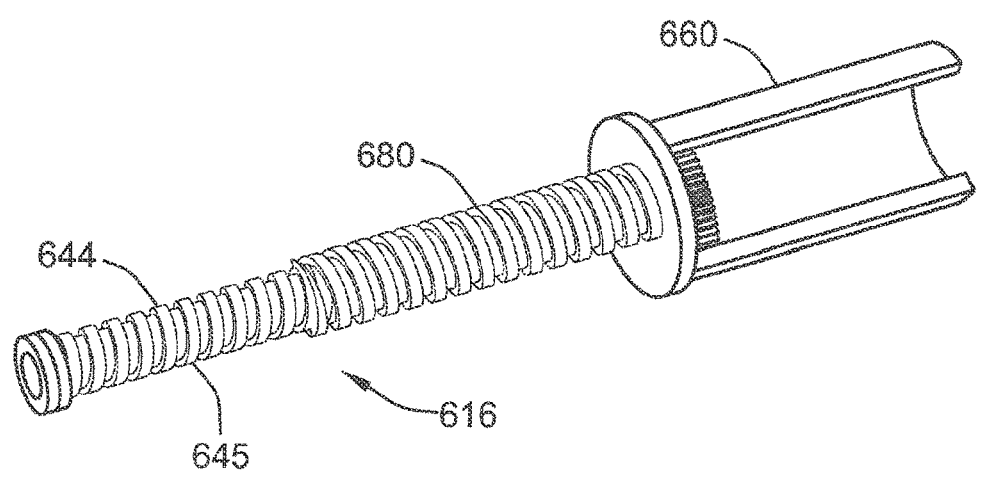
FIG. 8 illustrates a schematic view of a telescope piston rod arrangement illustrated in FIG. 7
Figure 9:
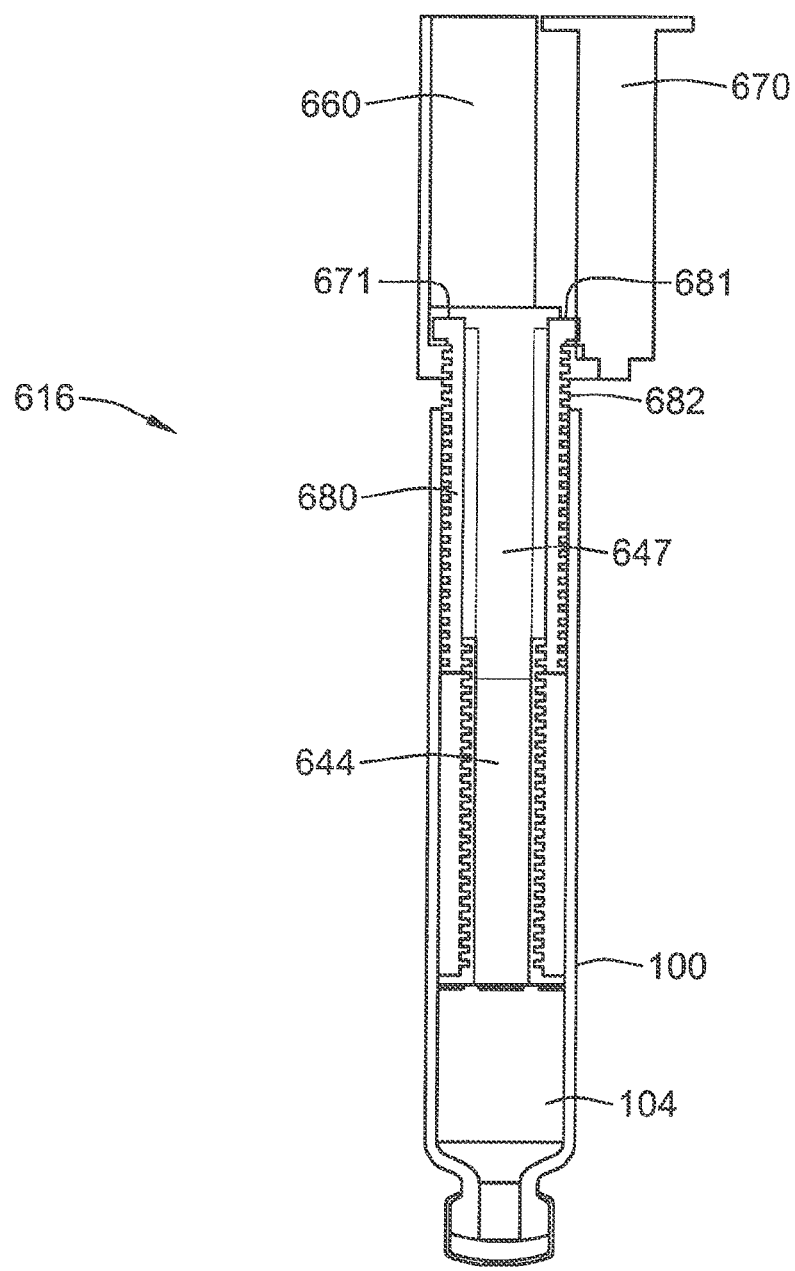
FIG. 9 illustrates a schematic view of one piston rod arrangement illustrated in FIG. 7.

The drive train telescoping piston rod 616 is illustrated in FIG. 7 and comprises a telescope plunger 644 that is operatively coupled to an input screw 680. FIG. 8 illustrates a perspective view of the telescope piston rod 616 coupled to a latch barrel. FIG. 9 illustrates a cross sectional view of the independent mechanical driver with the piston rod 616 in an extended position.

As illustrated, the outer elements (the telescope piston rod plunger 644 and telescope) represent the telescopic piston rod 616.

The transfer shaft 670 is operatively linked to the gearing arrangement 646. The transfer shaft 670 can rotate but it cannot move in an axial direction. As can be seen in FIG. 6, the transfer shaft 670 interfaces with the second gearing arrangement 646 and transfers the torque generated by the second gearbox arrangement 646 to the telescope piston rod 616.

Specifically, when the transfer shaft 670 is rotated by way of the gearing arrangement 646, the transfer shaft 670 will act on an integrated geared part 681 at a proximal end of the input screw 680. As such, rotation of the transfer shaft 670 causes the input screw 680 to rotate about its axis.

A proximal portion of the input screw 680 comprises a threaded section 682 and this threaded section is mated with a threaded section of the latch barrel 660. As such, when the input screw 680 rotates, it winds or screws itself in and out of the latch barrel 660. Consequently, as the input screw 680 moves in and out of the latch barrel, the screw 680 is allowed to slide along the transfer shaft 670 so that the transfer shaft and the gears remain mated.

The telescope plunger 644 is provided with a threaded section 645. This threaded section 645 is threaded into short section in the distal end of the input screw 680. As the plunger 644 is constrained from rotating, it will wind itself in and out along the input screw 680.

A key 647 is provided to prevent the plunger 644 from rotating. This key 647 may be provided internal to the input screw 680 of the piston rod 616. During an injection step, this key 647 moves in the axial direction towards the bung 104 of the cartridge 100 but does not rotate. The key 647 is provided with a proximal radial peg that runs in a longitudinal slot in the latch barrel 660. Therefore, the key 647 is not able to rotate. The key may also be provided with a distal radial peg that engage a slot in the plunger 644.

Preferably, the drug delivery device comprises memory devices comprising enough memory storage capability so as to store a plurality of algorithms that are used to define a plurality of different therapeutic profiles. In one preferred arrangement, after a user sets a dose of the primary medicament, the drug delivery device will be preprogrammed so as to determine or calculate a dose of the secondary medicament and perhaps a third medicament based on one of the stored therapeutic profiles. In one arrangement, the healthcare provider or physician selects a therapeutic dose profile and this profile may not be user alterable and/or may be password protected. That is, only a password known by the user, for example a healthcare provider or physician, will be able to select an alternative profile. Alternatively, in one drug delivery device arrangement, the dose profile is user selectable. Essentially, the selection of the therapeutic dose profiles can be dependent upon the individualized targeted therapy of the patient.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro- Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A medical device comprising:
   a reservoir,
   a bung,
   a piston,
   an electromechanical device, and
   a control unit,
   wherein said reservoir, said bung, said piston, and said electromechanical device are controlled by said control unit and are arranged such that said electromechanical device can be instructed to move said bung via said piston to eject a desired dose of fluid from said reservoir to a user during a single dose delivery process,
   wherein said control unit is configured to instruct the electromechanical device to move said bung via said piston over a first distance by a first advancing movement of said bung to eject part of said desired dose from said reservoir,
   wherein said control unit is configured such that said piston will be retracted by said electromechanical device after the control unit determines that a predetermined dwell time has elapsed following the first advancing movement of said bung,
   wherein the control unit is configured to determine whether the predetermined dwell time has elapsed for subsequent single dose delivery processes, and
   wherein said control unit is configured to turn off the electromechanical device for a non-zero time period after the first advancing movement and then instruct the electromechanical device to cause, within the dwell time, and after the non-zero time period, a second advancing movement of said bung via said piston over a second distance to eject a remainder of said desired dose from said reservoir.

2. The medical device according to claim 1, further comprising a gearing arrangement arranged such that said bung is moved by said electromechanical device by said gearing arrangement.

3. The medical device according to claim 1, said medical device being a drug delivery device and/or a portable medical device.

4. The medical device according to claim 1, wherein said electromechanical device is a stepper motor or a brushless DC-motor.

5. The medical device to according to claim 1, configured such that said dwell time can be variably adjusted.

6. The medical device according to claim 1, wherein said dwell time is at least 4 seconds.

7. The medical device according to claim 1, configured such that the first advancing movement of said bung accounts for a previous retraction of said piston.

8. The medical device according to claim 1, further comprising a motion detector configured such that:
   a backward movement of said electromechanical device is detected while said electromechanical device is turned off, and
   said second advancing movement is determined from said detected backward movement.

9. The medical device according to claim 1, further comprising:
   a second reservoir,
   a second bung, and
   a second piston,
   wherein the second reservoir, the second bung, the second piston, and the electromechanical device controlled by the control unit are arranged such that the electromechanical device can be instructed to move the second bung via the second piston over a third distance and a second fluid may be ejected from the second reservoir by an advancing movement of the second bung.

10. The medical device according to claim 1, further comprising:
    a second reservoir,
    a second bung,
    a second piston, and
    a second electromechanical device,
    wherein the second reservoir, the second bung, the second piston, and the second electromechanical device controlled by the control unit are arranged such that the second electromechanical device can be instructed to move the second bung via the second piston over a third distance and a second fluid may be ejected from the second reservoir by an advancing movement of the second bung.

11. The medical device according to claim 1, wherein said dwell time is at least 6 seconds.

12. The medical device according to claim 1, wherein said dwell time is at least 10 seconds.

13. The medical device of claim 1 wherein the control unit is provided with the predetermined dwell time such that the control unit does not need to calculate the dwell time.

* * * * *